US006493583B1

(12) United States Patent
Levine et al.

(10) Patent No.: US 6,493,583 B1
(45) Date of Patent: Dec. 10, 2002

(54) IMPLANTABLE CARDIAC STIMULATION DEVICE AND METHOD FOR TREATING INTRINSIC VENTRICULAR RHYTHMS ASSOCIATED WITH LOSS OF ATRIAL TRANSPORT

(75) Inventors: Paul A. Levine, Newhall, CA (US); G. Neal Kay, Birmingham, AL (US)

(73) Assignee: Pacesetter, Inc., Sylmar, CA (US)

( * ) Notice: Subject to any disclaimer, the term of this patent is extended or adjusted under 35 U.S.C. 154(b) by 183 days.

(21) Appl. No.: 09/641,000

(22) Filed: Aug. 17, 2000

(51) Int. Cl.[7] .............................................. A61N 1/362
(52) U.S. Cl. ........................................................ 607/9
(58) Field of Search ............................. 607/4, 9, 14, 25

(56) References Cited

U.S. PATENT DOCUMENTS

| | | | |
|---|---|---|---|
| 5,292,340 A | | 3/1994 | Crosby et al. ................. 607/17 |
| 5,376,106 A | | 12/1994 | Stahmann et al. ............. 607/18 |
| 5,466,254 A | | 11/1995 | Helland ....................... 607/123 |
| 5,643,326 A | | 7/1997 | Weiner et al. ................. 607/14 |
| 5,653,738 A | * | 8/1997 | Sholder ......................... 607/14 |
| 5,725,561 A | | 3/1998 | Stroebel et al. ................. 607/9 |
| 5,814,077 A | * | 9/1998 | Sholder et al. ................. 607/9 |
| 6,128,529 A | * | 10/2000 | Esler ............................. 607/4 |
| 6,330,477 B1 | * | 12/2001 | Casavant ..................... 607/14 |

OTHER PUBLICATIONS

Higano, Stuart T., et al., "Sensor–Driven Rate Smoothing in a DDDR Pacemaker", PACE, vol. 12, pp 922–929 (Jun. 1989).
Van Mechelen, R., et al., "Pacemaker Electrocardiography of Rate Smoothing During DDD Pacing", PACE, vol. 8, pp 684–690 (Sep.–Oct.).
Bode, Frank, et al., "Inhibition of Ventricular Stimulation in Patients with Dual Chamber Pacemakers and Prolonged AV Conduction", PACE, vol. 22, pp 1425–1431 (Oct. 1999).
Hayes, D.L., et al., "Electrocardiographic Manifestations of True Rate Smoothing with Sensor–Driven Rate Smoothing", European J.C.P.E., vol. 4, No. 2, pp 138–141 (1994).
Fisher, John D., M.D., et al., "Role of Implantable Pacemakers in Control of Recurrent Ventricular Tachycardia", The American Journal of Cardiology, vol. 49, pp 194–206 (Jan. 1982).
Simoncelli, Umberto, et al., "A Peculiar Form of Pacemaker Syndrome in DDD Pacing", International Journal of Cardiology, vol. 53, pp 90–93 (1996).
Barold, S. Serge, et al., "Optimal Pacing in First–Degree AV Block", PACE, vol. 22, pp 1423–1431 (Oct. 1999).
Barold, S. Serg, et al., Indicaitons or Permanent Cardiac Pacing in First–Degree AV Block: Class I, II, or III?, PACE, vol. 19, pp 747–751 (May 1996).
Levine, Paul A., M.D., et al., "Electrocardiography of Rate–Modulated Pacemaker Rhythms", Pacesetter©, pp 1–90 (1990).

* cited by examiner

Primary Examiner—Carl Layno

(57) ABSTRACT

An implantable cardiac stimulation device and method treats intrinsic ventricular rhythms lacking atrial transport to the heart. Once an arrhythmia detector detects an intrinsic ventricular rhythm lacking atrial transport, an atrial pulse generator paces the atria to restore atrial transport. The pacing is maintained at a constant rate for a first time period after which the pacing rate is decreased over a recovery time period. The device and method may also be employed for treating accelerated junctional rhythms, accelerated idioventricular rhythms, and first degree AV block, all of which result in inhibition of a dual-chamber pacemaker.

39 Claims, 3 Drawing Sheets

IMPLANTABLE CARDIAC STIMULATION DEVICE AND METHOD FOR TREATING INTRINSIC VENTRICULAR RHYTHMS ASSOCIATED WITH LOSS OF ATRIAL TRANSPORT

FIELD OF THE INVENTION

The present invention generally relates to an implantable cardiac stimulation device. The present invention more particularly relates to such a device and a method for treating an accelerated junctional rhythms, accelerated idioventricular rhythms, and marked first degree AV block, all of which may result in inhibition of a dual-chamber pacemaker leading to symptoms associated with the loss of appropriate atrioventricular synchrony and its associated atrial contribution to ventricular filling.

BACKGROUND OF THE INVENTION

Implantable cardiac stimulation devices are well known in the art. They include implantable pacemakers which provide stimulation pulses to a heart to cause a heart, which would normally or otherwise beat too slowly or at an irregular rate, to beat at a controlled normal rate. They also include defibrillators which detect when the atria and/or the ventricles of the heart are in fibrillation and apply cardioverting or defibrillating electrical energy to the heart to restore the heart to a normal rhythm. Implantable cardiac stimulation devices may also include the combined functionalities of a pacemaker and a defibrillator.

As is well known, implantable cardiac stimulation devices sense cardiac activity for monitoring the cardiac condition of the patient in which the device is implanted. By sensing the cardiac activity of the patient, the device is able to provide cardiac stimulation therapy when it is required.

In a healthy heart, the sinoatrial node (SA node) serves as the natural pacemaker of the heart. It is a group of specialized myocardial cells located on the posterior wall of the upper right atrium at the junction between the atrium and the superior vena cava. It initiates electrical impulses in the heart's myocardium at a more rapid rate than other myocardial cells.

The atrioventricular node (AV node) transmits electrical signals from the atria to the ventricles. It is a small concentration of specialized conductive tissue at the base of the atrial septum. The AV node serves an important role in maintaining atrioventricular synchrony, the sequence of an atrial depolarization followed by a ventricular depolarization after an appropriate PR interval. Maintenance of atrioventricular synchrony enhances cardiac output and the loss of it (loss of atrial transport) may reduce cardiac output by 10 to 30%. If the SA node fails, the AV node is capable of serving as a back-up pacemaker of the heart. However, the cardiac rate, under such circumstances, is generally lower than normal (40 to 60 beats per minute) and without atrial transport. However, in special circumstances, the junctional pacemaker may accelerate and usurp control from an otherwise normal sinus node. In the setting of sinus node dysfunction for which a pacemaker was implanted, the junctional focus may accelerate and usurp control from the otherwise normal dual-chamber pacemaker.

Accelerated junctional rhythms may occur as a consequence of AV nodal ablation, intrinsic disease involving the atrioventricular node or junction, as a consequence of metabolic imbalance or as a side effect of a multiplicity of medications.

Hence, patients with SA node dysfunction or who have had their AV node ablated generally have a demand pacemaker to regulate their heart rhythm. While such devices do regulate cardiac rhythm, these patients can experience accelerated junctional rhythms. These rhythms occur at a relatively high rate as a result of parasympathetic withdrawal or increased sympathetic stimulation. The intrinsic rhythm will be sensed by the pacemaker causing it to inhibit. The result is a loss of atrial transport. This abnormal rhythm may be associated with retrograde conduction to the atrium. In both circumstances, hemodynamics and cardiac output may be compromised. Also, under these conditions, the implanted demand pacemakers may be unable to provide assistance as the high rate may cause these devices to be inhibited.

A similar rhythm, but arising from a ventricular focus, is termed accelerated idioventricular rhythm (AIVR). It will have similar consequences with respect to compromising hemodynamics and for the patient who has a dual-chamber pacemaker, result in its inhibition. This rhythm may be associated with retrograde conduction.

A third rhythm is a sinus rhythm with marked first-degree AV block. At accelerated rates, the sinus P wave is appropriately tracked. However, in the setting of either an atrial premature beat that occurs so early as to coincide with the portion of the pacemaker's timing cycle where the atrial channel is refractory or a ventricular premature beat initiating a PVARP with the sinus beat thus coinciding with this refractory period, the P wave will not be tracked. However, if AV nodal conduction is intact, but with very slow conduction (a long time required to conduct from the atrium to the ventricle), the resulting native ventricular depolarization will cause the pacemaker to be inhibited. The result is that appropriate AV synchrony will be lost and the pacemaker will be inhibited.

In each of these three rhythms, there is an intrinsic ventricular rhythm effectively inhibiting the pacemaker yet each is associated with the loss of an optimal AV delay compromising cardiac function.

SUMMARY OF THE INVENTION

The present invention provides an implantable dual-chamber cardiac device and method for treating intrinsic ventricular rhythms lacking in atrial transport. A rhythm detector detects an intrinsic ventricular rhythm lacking in atrial transport when an R-wave detector detects a predetermined number of successive R-waves at a rate below a given rate and when each successive R-wave fails to be preceded by an atrial event, either intrinsic or paced.

When this rhythm is detected, an atrial pulse generator delivers an atrial pacing pulse to an atrium of the heart prior to each successive R-wave. The atrial pacing pulses are delivered an AV delay prior to the R-waves and the pacing rate is held constant for a time period. Thereafter, the pacing rate is gradually reduced during a recovery time period until a base rate is reached or until the end of the recovery time period.

If the period of AR pacing is supplanted by another intrinsic ventricular rhythm lacking in atrial transport, the device again begins delivering atrial output pulses at an appropriate time prior to the R-waves.

An intrinsic ventricular rhythm lacking atrial transport may also be detected by detecting successive R-waves succeeded by corresponding P-waves occurring during corresponding relative post-ventricular atrial refractory period intervals. When such a rhythm is detected, a pacing pulse is applied to an atrium a time period after each refractory sensed P-wave. The time period is selected to be sufficiently long to enable full recovery of the atria to render the pacing pulses effective in capturing the atria and restoring AV synchrony.

In accordance with the present invention, atrial transport is restored when the pulse generator would otherwise be inhibited. Further, the heart rate is returned to a more normal rate.

The device and method may further be used to treat intrinsic ventricular rhythms lacking atrial transport including accelerated junctional rhythms, accelerated idioventricular rhythms as well as marked first degree AV block that results in inhibition of a dual or multichamber pacing system. The present invention may be used to advantage in a stand-alone implantable dual-chamber pacemaker or in an implantable device having both a dual-chamber pacemaker and a cardioverter/defibrillator.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
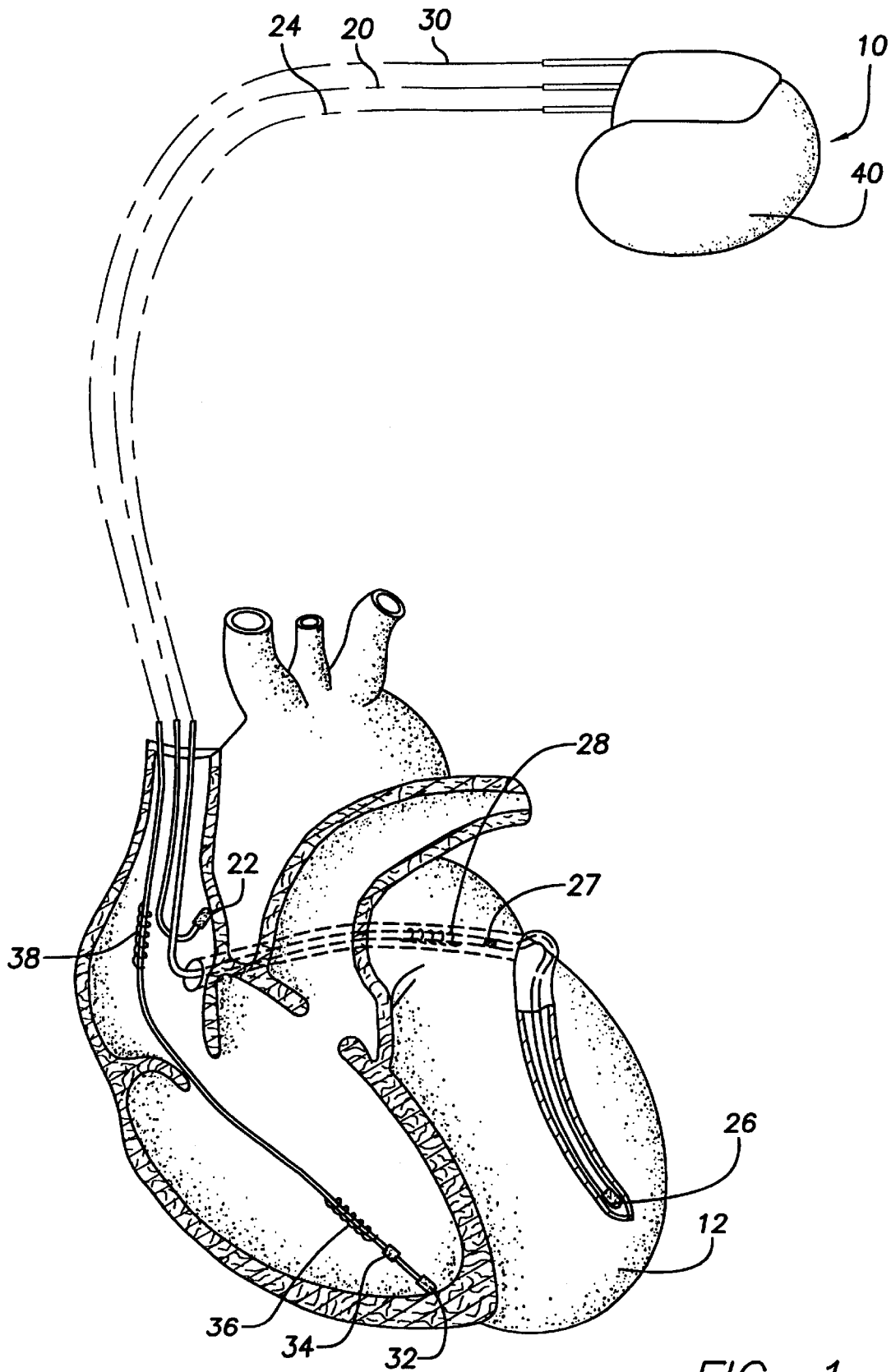
FIG. 1 is a simplified diagram illustrating an implantable cardiac stimulation device embodying the present invention.

As shown in FIG. 1, there is an implantable stimulation cardiac device 10 embodying the present invention. Although the device 10 described herein is a combined dual-chamber pacemaker and cardioverter/defibrillator having numerous leads, coil electrodes and pacing electrodes to provide both right and left heart dual-chamber pacing and atrial and ventricular cardioversion/defibrillation, it will be understood by those skilled in the art that this description is meant to illustrate the integrateability of the present invention into any implanted device providing dual-chamber pacing. Hence, the present invention may be employed to advantage in a dual-chamber pacing system having only atrial and ventricular unipolar electrodes or in a more sophisticated device of the type described herein. As a result, any reference to device function beyond that of dual-chamber pacing is made herein for purposes of completeness only.

The device 10 is in electrical communication with a patient's heart 12 by way of three leads, 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The electrode 22 may alternatively be positioned any place in the right atrium with the use of an active fixation lead or even in the left atrium with special leads.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Coronary sinus electrode refers specifically to left ventricular stimulation which will include epicardial leads placed directly on the surface of the left ventricle or left ventricular endocardial leads inserted via a patent foramen ovale or direct puncture of the interatrial septum.

Accordingly, the coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, filed Dec. 8 , 1999, titled "A Self-Anchoring, Steerable Coronary Sinus Lead" (Pianca et al.), which is a continuation-in-part of U.S. patent application Ser. No. 09/196,898, filed Nov. 20, 1998, now abandoned; and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
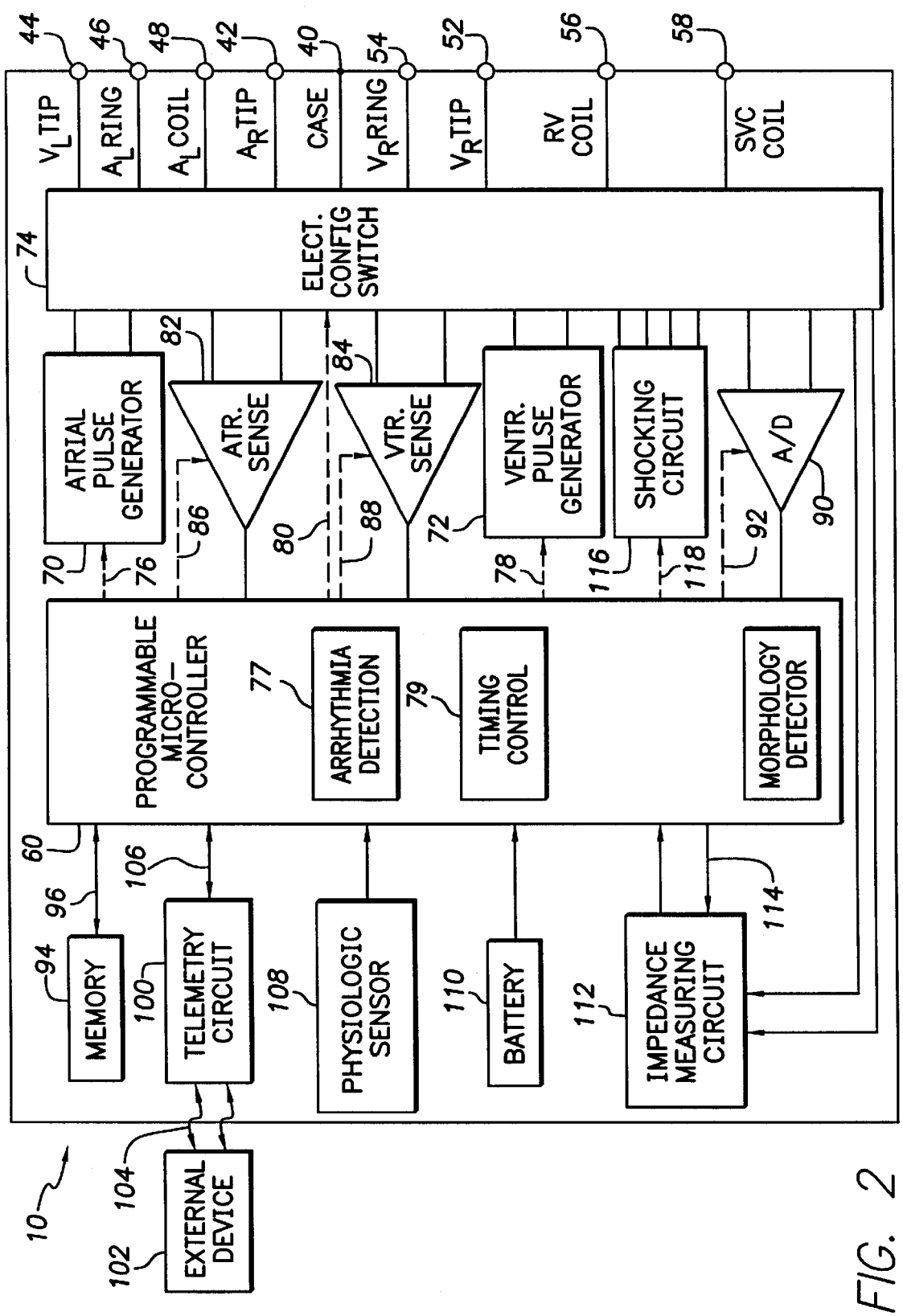
FIG. 2 is a functional block diagram of the device of FIG. 1 illustrating the basic elements of a stimulation device including those for delivering accelerated intrinsic ventricular rhythm therapy in accordance with a preferred embodiment of the present invention.

As illustrated in FIG. 2, a simplified block diagram is shown of the multi-chamber implantable stimulation device 10, which is capable of treating both fast and slow arrhythmias including accelerated junctional rhythms with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber (s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar"

modes. The housing 40 may further be used as a return electrode alone or in combination with one of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial tip electrode 22.

To achieve left chamber sensing, pacing and shocking, the connector includes at least a left ventricular tip terminal 44, a left atrial ring terminal 46, and a left atrial shocking terminal 48, which are adapted for connection to the left ventricular tip electrode 26, the left atrial tip electrode 27, and the left atrial coil electrode 28, respectively.

To support right chamber sensing, pacing and shocking, the connector further includes a right ventricular tip terminal 52, a right ventricular ring terminal 54, a right ventricular shocking terminal 56, and an SVC shocking terminal 58, which are adapted for connection to the right ventricular tip electrode 32, right ventricular ring electrode, 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals including relative post-ventricular atrial refractory period (RPVARP) intervals, noise detection windows, evoked response windows, alert intervals, marker channel timing, etc., which is well known in the art.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74 for detecting the presence of cardiac activity in each of the four chambers of the heart. Accordingly, the atrial and ventricular sensing circuits, 82 and 84, may include dedicated sense amplifiers, multiplexed amplifiers, or shared amplifiers. The switch bank 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity, respectively, in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the microcontroller 60 of device 10 provides arrhythmia detection 77 which utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

In accordance with the present invention, the arrhythmia detection 77 further detects intrinsic ventricular rhythms lacking transport, referred to also herein as transportless ventricular rhythms (TVR). Such a rhythm is preferably detected when a predetermined number of, for example, ten, successive R-waves are detected at a rate below a programmed given rate but above a base rate, wherein each successive R-wave fails to be preceded by a P-wave or atrial pacing. In this event, atrial transport is deemed to be lost at a rate above a base rate and TVR therapy is initiated as described subsequently. The programmed given rate above the base rate may be, for example, 100 beats per minute (bpm) and the base rate may be, for example, 60 bpm.

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 employs lithium/silver vanadium oxide batteries, as is true for most (if not all) such devices to date.

As further shown in FIG. 2, the device 10 is shown as having an impedance measuring circuit 112 which is enabled by the microcontroller 60 by a control signal 114. The impedance measuring circuit 112 is not critical to the present invention and is shown for only completeness.

To provide the function of an implantable cardioverter/defibrillator (ICD) the device must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
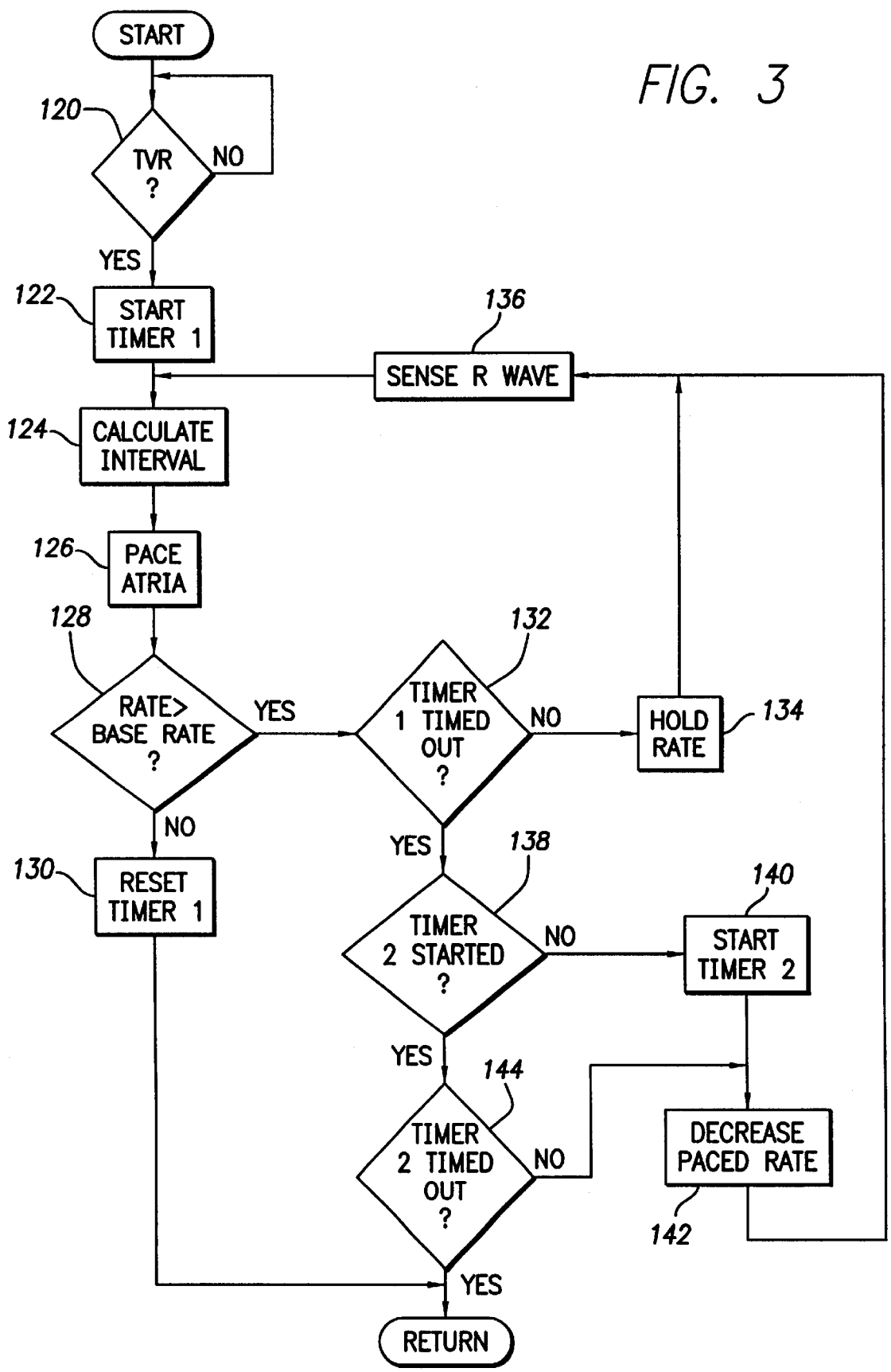
FIG. 3 is a flow chart describing an overview of the operation of one embodiment of the present invention.

In FIG. 3, a flow chart is shown describing an overview of the operation and novel features implemented in one embodiment of the device 10. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 initiates with a decision block 120. In decision block 120, the arrhythmia detection 77 of microcontroller 60 determines if a transportless ventricular rhythm (TVR) has been detected. Decision block 120 may be implemented as previously described. If a TVR has been detected, the microcontroller advances to activity block 122 and starts a first timer. The first timer times a time period wherein pacing is maintained or held at the current heart rate. The pacing may be, for example, standard dual-chamber pacing (DDD, or DDI) with or without rate modulation by physiologic sensor 108.

The process next advances to activity block 124 wherein the last cardiac interval, the interval between the last two consecutive R-waves, is calculated. From this interval, the microprocessor then subtracts an AV interval, based upon the calculated cardiac interval to determine an RA interval from the last detected R-wave. At the end of the RA interval, the microcontroller then causes an atrium, such as the right atrium, to be paced, for inserting an atrial pacing pulse an AV delay before the next R-wave. In this manner, the therapy reestablishes atrial transport.

After the atria are paced in activity block 126, the microcontroller then determines in decision block 128 if the heart rate, based upon the last calculated cardiac interval, has returned to a basic rate. As the therapy is newly initiated at this time, it is likely that the rate will be above the base rate and the process advances to decision block 132.

In decision block 132, the microcontroller determines if the first timer has timed out. The time period timed by the first timer wherein the pacing rate is held constant may be, for example, on the order of one minute. If the first timer has not timed out, the process advances to activity block 134 for holding the pacing rate at the rate existing upon detection of the AJR. The process then proceeds to activity block 136 for sensing the next R-wave. After the next R-wave is sensed, the foregoing process is repeated until either the rate falls below the basic rate, as determined in decision block 128 at which time the first timer is reset in activity block 130 and the process returns, or until the first timer times out as determined in decision block 132.

If the therapy continues to the timing out of the first timer without the rate falling below the basic rate, the process then advances to decision block 138 wherein it is determined if a second timer has been started. If it hasn't, the second timer is started in activity block 140. The second timer times a recovery time period during which the pacing rate is decremented at each pass through to return the heart rate to the basic rate. The recovery time period may be a programmed recovery time if rate modulation is enabled or the longest available recovery time if rate modulation is disabled. In either case, the recovery time period may be on the order of five minutes, as an example. Preferably, the rate decrementations are selected for returning the heart rate to the basic rate by the end of the recovery time period.

Once the second timer is started in activity block 140, the process advances to activity block 142 wherein the current pacing rate is decreased or decremented. The process then returns to activity block 136 for sensing the next R-wave, calculating a new cardiac interval and RA interval (activity block 124) and inserting an atrial pacing pulse (activity block 126) an AV delay before the next R-wave. The sequence of maintaining atrial transport at a gradually decreasing pacing rate continues until either the intrinsic rate falls below the basic rate, as determined in accordance with decision block 128, or until decision block 144 determines that the second timer has timed out, at which time the process returns. Of course, if a TVR remains after the process returns, the TVR therapy is reinitiated.

In accordance with further aspects of the present invention, the capability of detecting atrial events occurring within a relative post-ventricular atrial refractory period (RPVARP) may be utilized to advantage. Patients with junctional rhythms commonly have retrograde conduction. Retrograde conduction causes an R-wave to be conducted back to the atrial causing an atrial activation during the PVARP. If this occurs during the RPVARP, it will be sensed as a P-wave, but not tracked. Hence, if there is a stable detected R-wave to retrograde conduction P-wave rhythm determined in decision block 120, activity block 124 may be implemented such that an atrial output will be delivered an interval after the retrograde conduction P-wave, but before the next R-wave, to assure that the atria have fully recovered. Otherwise, the atria will still be refractory and the output will be ineffective in restoring AV synchrony. The interval may be, for example, 300 to 560 ms to assure complete recovery of the atria.

A similar situation presents itself for patients who have dramatic first degree AV block. Here, P-waves are conducted to the ventricles but at a much slower rate than normal. The situation may develop where a P-wave occurs during the PVARP and is not tracked. However, the P-wave is conducted, albeit slowly, causing an R-wave to occur prior to the time out of the atrial escape interval to inhibit the atrial output. The next P-wave occurs in the PVARP and again conducts sustaining pacemaker inhibition. Even though there is intact AV nodal conduction, the coincidence of the P-wave within the PVARP results in the loss of atrial transport and is hemodynamically equivalent to retrograde conduction. If the P-waves occur during the RPVARP, where they may be sensed the arrhythmia detector 77 will determine in decision block 120 that a transportless intrinsic ventricular rhythm exists wherein P-waves are sensed during RPVARP to cause activity block 124 to again be implemented to time an atrial output to be delivered to a coupling interval of 300 to 350 ms after the P-waves sensed during the RPVARP. While this may cause a first atrial output to be delivered at an interval shorter than a programmed AV delay, the atrial output will still be delivered prior to the next R-waves, capture the atria, and potentially inhibit or reset the intrinsic atrial mechanism allowing restoration of a physiologic AV interval on subsequent cardiac cycles.

As may thus be seen from the above, relative post-ventricular atrial refractory period may be used to advantage. The delivered atrial output will cause an atrial depolarization rendering the atrium refractory on a physiologic basis and preclude retrograde conduction (junctional and AIVR rhythms) or reset the intrinsic sinus mechanism and restore AV synchrony (in the presence of first degree AV block).

As can thus be seen from the foregoing, the present invention provides a therapy for accelerated intrinsic ventricular rhythms where there is a loss of appropriate AV synchrony. The therapy reestablishes atrial transport when it would have been otherwise lost and returns the heart to a safe lowered rate without compromising hemodynamics and cardiac output.

The foregoing therapy may also be effective in restoring AV synchrony in the setting of an accelerated idioventricular rhythm (AIVR). AIVR often occurs in pathologic conditions such as acute myocardial infarctions due to primary increases in automaticity of a pacemaker focus located in the ventricle or a local area of reentry in the ventricle. The present invention provides an effective alternative to treat such conditions without resorting to medications which accelerate the normal sinus mechanism to overdrive the accelerated ectopic focus instead of suppressing it but at the same time, increasing the metabolic demand of the myocardium and potentially aggravating an ischemic condition. It can also address the loss of appropriate AV synchrony in the setting of first degree AV block.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device for treating an intrinsic ventricular rhythm of a heart lacking atrial transport, comprising:
   a rhythm detector that detects an intrinsic ventricular rhythm of the heart lacking atrial transport; and
   an atrial pulse generator that delivers, responsive to detection of an intrinsic ventricular rhythm of the heart lacking atrial transport, an atrial pacing pulse to an atrium of the heart prior to each R-wave of the heart.

2. The device of claim 1 further including a pacing rate control circuit that decreases the pacing rate of the atrial pulse generator over a recovery time period.

3. The device of claim 1 wherein the atrial pulse generator is further configured to pace the atria on demand, wherein the device further includes an R-wave detector and a P-wave detector, wherein the intrinsic ventricular rhythm lacking atrial transport is a transportless ventricular rhythm, and wherein the rhythm detector detects a transportless ventricular rhythm when the R-wave detector detects a predetermined number of successive R-waves at a rate below a given rate and when each successive R-wave fails to be preceded by a P-wave or atrial pacing.

4. The device of claim 1 wherein the atrial pulse generator is further configured to pace the atria on demand, wherein the device further includes an R-wave detector and a P-wave detector, wherein the ventricular rhythm lacking transport is a transportless ventricular rhythm, and wherein the rhythm detector detects a transportless ventricular rhythm when the R-wave detector detects a predetermined number of successive R-waves at a rate above a base rate and below a given rate.

5. The device of claim 2 wherein the pacing rate control circuit maintains the pacing rate at a constant rate for a first time period prior to decreasing the pacing rate.

6. The device of claim 5 further including a first timer that times the first time period.

7. The device of claim 2 further including a timer that times the recovery time period.

8. The device of claim 3 further including an interval determining circuit that determines cardiac intervals between successive R-waves.

9. The device of claim 8 wherein the atrial pulse generator delivers each atrial pacing pulse an RA delay after each detected R-wave.

10. The device of claim 9 wherein each RA delay equals an immediately preceding cardiac interval minus an AV delay.

11. The device of claim 1 further including a timer that times relative post-ventricular atrial refractory period intervals and wherein the rhythm detector detects an intrinsic ventricular rhythm lacking atrial transport responsive to occurrence of successive R-waves succeeded by corresponding P-waves occurring during corresponding relative post-ventricular atrial refractory period intervals.

12. The device of claim 11 wherein the atrial pulse generator delivers an atrial pacing pulse to an atrium of the heart an interval after each P-wave occurring during a relative post-ventricular atrial refractory period interval.

13. The device of claim 12 wherein the interval is between 200 and 550 milliseconds.

14. An implantable cardiac stimulation device for treating an intrinsic ventricular rhythm lacking atrial transport of a heart comprising:
  rhythm detecting means for detecting an intrinsic ventricular rhythm lacking atrial transport of the heart; and
  stimulation means, responsive to the rhythm detecting means detecting an intrinsic ventricular rhythm lacking atrial transport, for delivering stimulation pulses to an atrium of the heart prior to R-waves of the heart.

15. The device of claim 14 wherein the device further includes R-wave detecting means for detecting R-waves of the heart and P-wave detecting means for detecting P-waves of the heart, and wherein the rhythm detecting means is responsive to the R-wave detecting means detecting a predetermined number of successive R-waves at a rate below a given rate with each of the successive R-waves failing to be preceded by a detected P-wave or atrial pacing for detecting an intrinsic ventricular rhythm lacking atrial transport.

16. The device of claim 14 wherein the device further includes R-wave detecting means for detecting R-waves of the heart and P-wave detecting means for detecting P-waves of the heart, and wherein the rhythm detecting means is responsive to the R-wave detecting means detecting a predetermined number of successive R-waves at a rate above a base rate and below a given rate with each of the successive R-waves failing to be preceded by a detected P-wave or atrial pacing for detecting an intrinsic ventricular rhythm lacking atrial transport.

17. The device of claim 15 further including control means for maintaining the stimulation rate of the stimulation means at a constant rate for a first time period.

18. The device of claim 17 further including a first timing means for timing the first time period.

19. The device of claim 17 wherein the control means decreases the stimulation rate of the stimulation means during a recovery time period following the first time period.

20. The device of claim 19 further including second timing means for timing the recovery time period.

21. The device of claim 15 further including interval determining means for determining cardiac intervals between successive R-waves.

22. The device of claim 21 wherein the stimulation means delivers each atrial pacing pulse an RA delay after each detected R-wave.

23. The device of claim 22 wherein each RA delay equals an immediately preceding cardiac interval minus an AV delay.

24. The device of claim 14 further including timing means for timing relative post-ventricular atrial refractory period intervals and wherein the rhythm detecting means detects an intrinsic ventricular rhythm lacking atrial transport responsive to occurrence of successive R-waves succeeded by corresponding P-waves occurring during corresponding relative post-ventricular atrial refractory period intervals.

25. The device of claim 24 wherein the stimulation means delivers an atrial stimulation pulse to an atrium of the heart an interval after each P-wave occurring during a relative post-ventricular atrial refractory period interval.

26. The device of claim 25 wherein the interval is between 200 and 550 milliseconds.

27. In an implantable cardiac stimulation device, a method of treating an intrinsic ventricular rhythm lacking atrial transport of a heart, the method including the steps of:
  detecting an intrinsic ventricular rhythm lacking atrial transport;
  applying an atrial pacing pulse to an atrium of the heart prior to each R-wave of the heart.

28. The method of claim 27 including the further step of terminating the applying step after a recovery period.

29. The method of claim 28 wherein the applying step includes applying the pacing pulses at a decreasing rate during the recovery period.

30. The method of claim 29 wherein the applying step includes applying the pacing pulses at a fixed rate for a time period prior to decreasing the rate.

31. The method of claim 30 wherein the time period is a fixed time period.

32. The method of claim 31 including the further step of timing the recovery period immediately after the time period.

33. The method of claim 27 wherein the detecting step includes detecting a predetermined number of successive R-waves of the heart at a rate below a given rate with each successive R-wave failing to be preceded by a P-wave of the heart.

34. The method of claim 27 wherein the detecting step includes detecting a predetermined number of successive R-waves of the heart at a rate above a base rate and below a given rate with each successive R-wave failing to be preceded by a P-wave of the heart.

35. The method of claim 33 wherein the applying step includes applying each atrial pacing pulse an RA interval after each detected R-wave.

36. The method of claim 35 including the further step of determining cardiac intervals between successive R-waves and wherein the RA interval equals a preceding cardiac interval minus an AV delay.

37. The method of claim 27 further including the step of timing relative post-ventricular atrial refractory period intervals and wherein the step of detecting an intrinsic ventricular rhythm lacking atrial transport includes detecting successive R-waves succeeded by corresponding P-waves occurring during corresponding relative post-ventricular atrial refractory period intervals.

38. The method of claim 37 wherein the applying steps includes delivering a stimulation pulse to the atrium of the heart an interval after each P-wave occurring during a relative post-ventricular atrial refractory period interval.

39. The method of claim 38 wherein the interval is between 200 and 550 milliseconds.

* * * * *